United States Patent [19]

Kimura et al.

[11] Patent Number: 5,089,529
[45] Date of Patent: Feb. 18, 1992

[54] BUTANOL DERIVATIVES

[75] Inventors: Kiyoshi Kimura; Takeshi Yamaguchi, both of Takatsuki; Iwao Morita; Tetsuo Murakami, both of Kyoto, all of Japan

[73] Assignee: Nippon Shinyaku Co., Ltd., Japan

[21] Appl. No.: 673,947

[22] Filed: Nov. 21, 1984

[30] Foreign Application Priority Data

Nov. 21, 1983 [JP] Japan ................. 58-220342

[51] Int. Cl.$^5$ ............... A61K 31/135; C07C 215/08
[52] U.S. Cl. .................. 514/648; 514/554; 564/320; 564/324
[58] Field of Search ............. 564/320, 324; 514/554, 514/648

[56] References Cited

U.S. PATENT DOCUMENTS

| | | | |
|---|---|---|---|
| 2,441,664 | 11/1946 | Mischer et al. | 564/320 X |
| 2,682,543 | 6/1954 | Adamson et al. | 564/320 X |
| 3,190,920 | 6/1985 | Spickett et al. | 564/320 |
| 3,441,602 | 4/1969 | Hollinger et al. | 564/320 X |

FOREIGN PATENT DOCUMENTS

| | | | |
|---|---|---|---|
| 256801 | 1/1963 | Australia | 564/320 |
| 269705 | 4/1964 | Australia | 564/320 |

OTHER PUBLICATIONS

Barton et al., "Synthetic Analgesics", Part I, Diphenylpropylamines, vol. 3, pp. 110–114 (1960).
Wolf, "Burgar's Medicinal Chemistry", 4th ed., Part III, pp. 84–89 (1979).

*Primary Examiner*—Richard L. Raymond
*Attorney, Agent, or Firm*—Rosenman & Colin

[57] ABSTRACT 4-mono- and di-isobutylamino butanols of the formula (I):

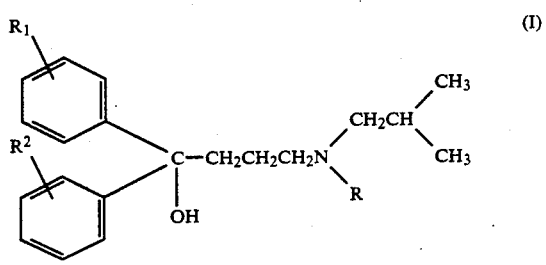

or a pharmaceutically acceptable salt thereof wherein $R^1$ and $R^2$ are the same or different and each is selected from the group consisting of hydrogen, halo, hydroxyl, alkyl of 1 to 4 carbon atoms and alkoxy of 1 to 4 carbon atoms and R is hydrogen or isobutyl, are useful for the treatment of circulatory disorders, particularly arrhythmias, in humans and animals.

7 Claims, No Drawings

BUTANOL DERIVATIVES

The present invention is concerned with 4-Mono- and Di-isobutyl aminobutanol derivatives and pharmaceutically acceptable salts thereof which are useful in the treatment of circulatory disorders, in particular arrhythmias. Pharmaceutical compositions containing said compounds as the active agent and methods of use thereof and processes for their production thereof all form part of the present invention.

More particularly, the present invention is concerned with 4-mono- and di-isobutylaminobutanol derivatives of the formula (I):

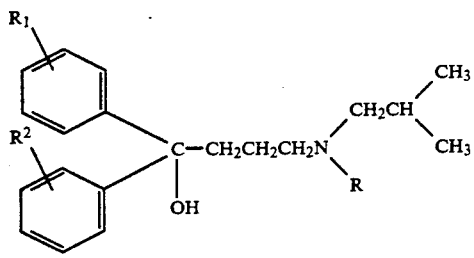

or a pharmaceutically acceptable salt thereof wherein $R^1$ and $R^2$ are the same or different and each is selected from the group consisting of hydrogen, halo, hydroxyl, alkyl of 1 to 4 carbon atoms and alkoxy of 1 to 4 carbon atoms and R is hydrogen or isobutyl. These compounds have been found to be useful for the treatment of circulatory disorders, particularly arrhythmias, as they have been found to have far better anti-arrhythmic action and much lower toxicity than known anti-arrhythmic agents.

According to one embodiment of the present invention, $R^1$ and $R^2$ are the same or different and each is selected from the group consisting of hydrogen, fluoro, chloro, bromo, iodo (especially fluoro, chloro or bromo), hydroxyl, alkyl of 1 to 4 carbon atoms and alkoxy of 1 to 4 carbon atoms.

According to a further embodiment of the present invention, $R^1$ and $R^2$ are the same or different and each is selected from the group consisting of hydrogen, fluoro, chloro, bromo, hydroxyl, methyl, ethyl, propyl, isopropyl, tert-butyl, methoxy, ethoxy and propoxy.

In addition to the compounds of the examples set forth below, the following compounds are representative of those of the present invention:
1,1-Bis(2-chlorophenyl)-4-diisobutylamino-1-butanol,
1,1-Bis(2-fluorophenyl)-4-diisobutylamino-1-butanol,
1-(2-Chlorophenyl)-4-diisobutylamino-1-phenyl-1-butanol,
1-(2-Fluorophenyl)-4-diisobutylamino-1-phenyl-1-butanol,
1,1-Bis(4-Bromophenyl)-4-diisobutylamino-1-butanol,
1,1-Bis(4-Hydroxyphenyl)-4-diisobutylamino-1-butanol,
1-(4-Hydroxyphenyl)-4-diisobutylamino-1-phenyl-1-butanol,
1,1-Bis(4-tert-butylphenyl)-4-diisobutylamino-1-butanol,
1,1-Bis(4-ethylphenyl)-4-diisobutylamino-1-butanol, or
1,1-Bis(4-ethoxyphenyl)-4-diisobutylamino-1-butanol.

The present invention also includes a process for the production of the 4-mono- and di-isobutylaminobutanol derivatives of formula (I). Processes (1)–(3) are for the production of compounds of formula (I) wherein R is isobutyl and process (4) is for the production of compounds of the formula (I) wherein R is hydrogen.

According to the process of the present invention compounds of the formula (I) are produced by:

1) reacting an amino ester of the formula (II):

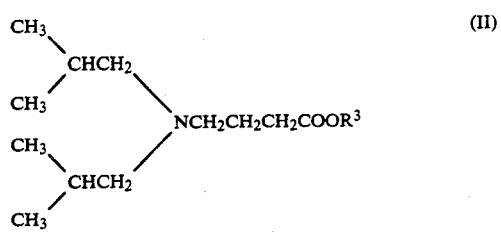

wherein $R^3$ is lower alkyl with a Grignard reagent of the formula (III):

wherein $R^1$ is hydrogen, halo, hydroxyl, alkyl of 1 to 4 carbon atoms or alkoxy of 1 to 4 carbon atoms and X is halo or with a lithium compound of the formula (IV):

wherein $R^1$ is a above defined;

2) reacting a compound of the formula (V):

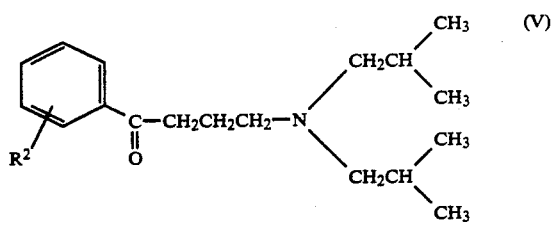

wherein $R^2$ is hydrogen, halo, hydroxyl, alkyl of 1 or 4 carbon atoms or alkoxy of 1 to 4 carbon atoms with a compound of the formula (III):

or (IV):

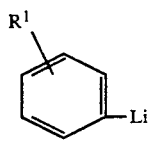

wherein $R^1$ is as above defined;

3) reacting a benzophenone of the formula (VI):

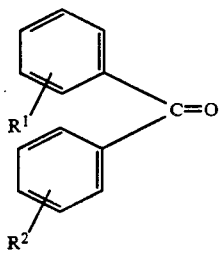

wherein $R^1$ and $R^2$ are as above defined with a Grignard reagent of the formula (VII):

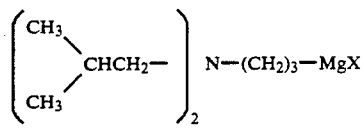

wherein X is halo or with a lithium compound of the formula (VIII):

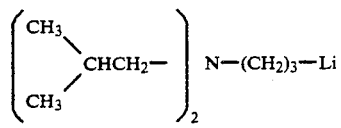

or 4) reacting a benzoylpropionate of the formula (XII):

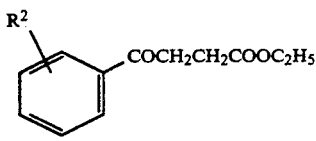

wherein $R^2$ is as above defined with a Grignard reagent of the formula (III):

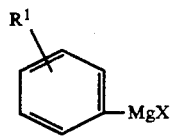

wherein $R^1$ is as above defined or with a lithium compound of the formula (IV):

wherein $R^1$ is as above defined to produce a compound of the formula (XIII):

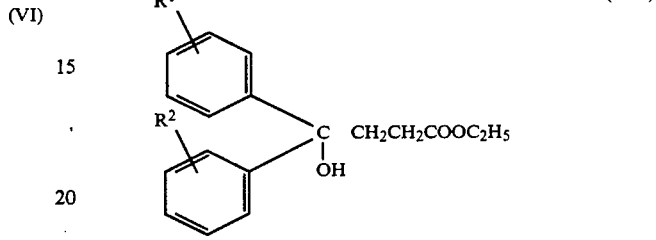

wherein $R^1$ and $R^2$ are as above defined, which is then reacted with isobutylamine to produce a compound of the formula (XIV):

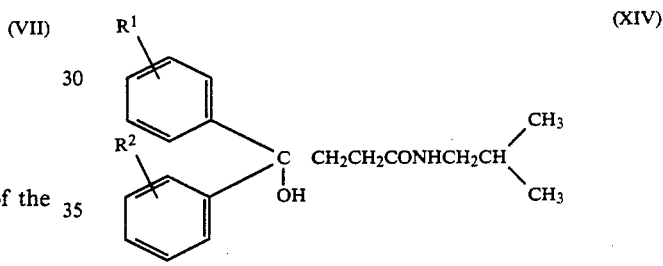

wherein $R^1$ and $R^2$ is as above defined, reducing said compound to produce a compound of the formula (XV):

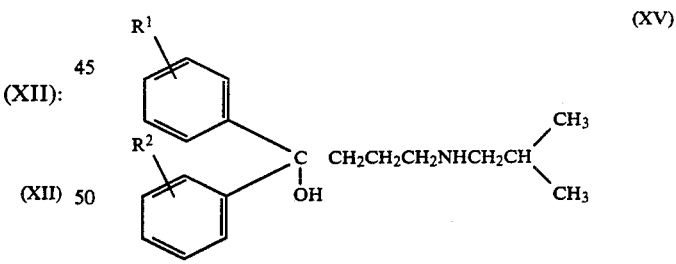

wherein $R^1$ and $R^2$ are as above defined.

Grignard reagents wherein X is halo which are used in reactions 1), 2) and 3) above can be readily prepared by methods per se known in the art for the preparation of Grignard reagents. The most preferred solvents are anhydrous ether, tetrahydrofuran, isopropyl ether, dioxane, dimethoxyethane, diethyleneglycol, dimethyl ether and other ether type solvents and hydrocarbon type solvents such as benzene, toluene, pentane, n-hexane and petroleum ether. Amines may also be used. The reaction proceeds more smoothly when reaction initiators such as iodine, ethyl bromide and dibromoethane are added. Reaction temperature is preferably in the range of from about 0° C. to about 100° C.

The lithium compounds used in processes 1), 2) and 3) can also be readily manufactured by procedures per se known in the art for the production of organic lithium compound synthesis. Preferred solvents in the reaction are the same as those for the preparation of Grignard reagents and in addition, hexamethylenephosphoric triamide (HMPA), N,N'-dimethylimidazolidinone (DMI) and the like. It is possible to activate the reaction by the addition of amines such as N,N'-tetramethylethylenediamine or large ring ethers, i.e. crown ethers. Reaction temperature is preferably within the range of from about −78° C. to about +100° C.

Generally, the Grignard reagents and the lithium compounds are used directly as prepared, that is in the form of solutions and are added at the appropriate stage, for example to the reaction with ketones and esters. The amount of ketones and esters used in the reaction is generally from about 1.0 to about 0.8 equivalent to the Grignard reagent or to the lithium compound. It is preferred that the ketones or esters are added after they are dissolved in a small amount of the same solvent. The reaction temperature is preferably from about −78° C. to about +100° C. and more preferably from about −20° C. to about +50° C. The reaction is generally complete within 30 minutes to five hours.

After the reaction is complete, the reaction solution is treated by conventional procedures. For example, after the Grignard reagent reaction is complete, the reaction mixture is washed with an aqueous solution of ammonium chloride, then with an aqueous solution of sodium bicarbonate and then washed with water.

Following such a treatment, the resulting crude base is usually crystallized and then purified by recrystallization. When crystallization is not possible, the product is treated with an acid and is crystallized as a salt. Further purification can be accomplished by recrystallization. When crystallization is still not possible, the reaction mixture is purified by column chromatography and then crystallized if necessary by conversion to a salt and then recrystallization to give the desired compound in pure form.

The starting material (II) can be produced from ethyl gamma-chlorobutyrate and diisobutylamine. Starting material (V) can be prepared in the following manner. An excess of diisobutyl amine is reacted with gamma-chlorobutyrophenone ethyleneketal for about 13 hours in the presence of sodium iodide. The resulting aminoketal is then heated in a hydrochloric acid solution to hydrolyze and is made basic by the addition of an alkali.

Starting materials (VII) and (VIII) may be produced from 3-diisobutylaminopropyl chloride by conventional procedures well known in the art. The other starting materials are readily available or can be produced by one skilled in the art from commercially available substances.

The Grignard reagent and lithium compounds used for process (4) can be prepared by the same methods already described with reference to processes (1), (2) and (3). Starting material (XII) can be produced by procedures per se known in the art. Intermediate (XIV) can be produced by treating compound (XIII) with isobutylamine in a suitable solvent, for example xylene, to toluene, N,N-dimethyl formamide, dioxane or in the absence of solvents at a temperature of from about 80° C. to 150° C., more preferably from about 100° C. to about 110° C. Intermediate (XIV) can be reduced, for example by the addition of ithium aluminum hydride in a suitable solvent, for example tetrahydrofuran, dioxane or ether to give (XV).

The compounds of the formula (I) may be in in the form of the free base or an acid addition salt. The acid addition salt may be with an inorganic or organic acid. The acid addition salt is preferably a pharmaceutically acceptable one. Typical acid addition salts are formed with acids such as hydrochloric acid, hydrobromic acid, sulphuric acid, sulfamic acid, phosphoric acid, acetic acid, citric acid, tartaric acid, succinic acid, maleic acid, fumaric acid, lactic acid, malic acid, gluconic acid, methanesulfonic acid, p-toluenesulfonic acid, benzoic acid and pamoic acid.

The present invention also includes pharmaceutical compositions useful for treating arrhythmias in humans and animals which comprise an anti-arrhythmic amount of the formula (I):

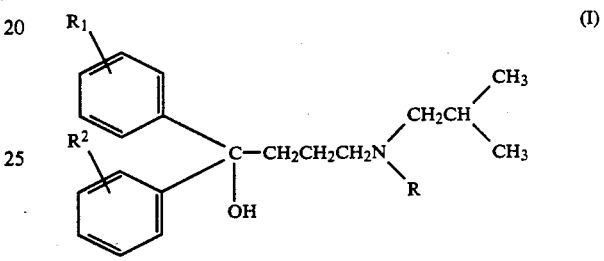

or a pharmaceutically acceptable salt thereof wherein $R^1$ and $R^2$ are the same or different and each is selected from the group consisting of hydrogen, halo, hydroxyl, alkyl of 1 to 4 carbon atoms and alkoxy of 1 to 4 carbon atoms and R is hydrogen or isobutyl, in combination with a pharmaceutically acceptable carrier. $R^1$, $R^2$ and R are as above defined with respect to compounds of the formula (I).

The present invention also includes a method of treating circulatory disorders, particularly arrhythmias, in humans and animals which comprises administering to a human or animal in need thereof an anti-arrhythmic amount of a compound of the formula (I):

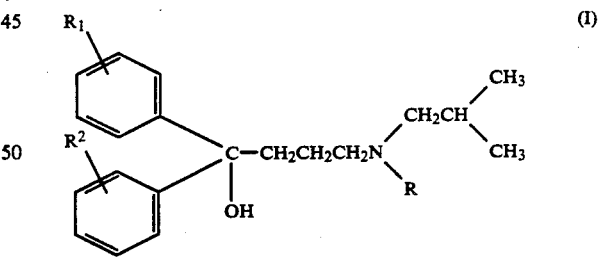

or a pharmaceutically acceptable salt thereof Wherein $R^1$ and $R^2$ are the same or different and each is selected from the group consisting of hydrogen, halo, hydroxyl, alkyl of 1 to 4 carbon atoms and alkoxy of 1 to 4 carbon atoms and R is hydrogen or isobutyl, in combination with a pharmaceutically acceptable carrier.

When the pharmaceutical compositions of the present invention are administered to humans and animals, they preferably contain from about 0.1 to about 99.5% and more preferably from about 1% to about 80% of a compound of the formula (I) or a pharmaceutically acceptable salt thereof, in combination with a pharmaceutically acceptable carrier.

Examples of the carriers applicable are one or more of solid, semi-solid or liquid diluents, fillers and other pharmaceutical auxiliary agents. It is desired that the pharmaceutical preparations are administered in unit dosage form. Pharmaceutical compositions of the present invention may be administered per os, into tissue, locally (such as via skin) or rectally. Administration is conducted by a form suitable for each route, for example, injection is especially preferred.

It is desired that the dose is regulated after considering the state of the patients such as age, body weight, etc., administration route and the nature and degree of the diseases but usually the range of 1 to 3000 mg of a compound of the present invention per day for an adult human is common and the range of 10 to 1000 mg is preferred. Of course, in some cases it is sufficient even below the above range and in other cases a greater dosage may be required. When a larger dose is given, it is desired that the compound be given dividedly, i.e. several times per day.

Oral administration is carried out by a solid or liquid dosage unit form such as, for example, pure powder, diluted powder, tablets, sugar coated tablets, capsules, granules, suspensions, liquid, syrups, drops, sublingual tablets, etc.

Pure powder is manufactured by making the active substance into suitable fine size. Diluted powder is manufactured by making the active substance into suitable fine size and then mixing with similarly fine carriers such as starch, mannitol and other edible hydrocarbons. If necessary, seasoning agents, preservatives, dispersion agents, coloring agents, perfumes and the like may be mixed therewith.

Capsules are manufactured as follows. Pure powder or diluted powder in powdery form as above or granules as illustrated in the entry of tablets are filled in outer capsules such as, for example, gelatine capsules. It is of course possible to mix the powdery substances with lubricants or fluidizing agents such as, for example, colloidal silica, talc, magnesium stearate, calcium stearate, solid polyethylene glycol and the like followed by conducting the filling operation. Addition of disintegrating agents or solubilizing agents such as, for example, carboxymethyl cellulose, carboxymethyl cellulose calcium, hydroxypropyl cellulose with low degree of substitution, calcium carbonate, sodium carbonate and the like are effective in improving the effectiveness of the pharmaceuticals when capsules are taken.

Finely powdered compounds of the present invention may also be suspended and dispersed in vegetable oil, polyethylene glycol, glycerine, surface active agents, and the like and packed with gelatine sheets to afford soft capsules.

Tablets are manufactured by first preparing powdery mixture, then made into granules or slugs, mixed with disintegrating agents or lubricants and then made into tablets.

Powdery mixtures are prepared by mixing a suitably pulverized substance with the above-given diluents or bases followed, if necessary, by mixing with combining agents (such as sodium carboxymethyl cellulose, alginates, gelatine, polyvinyl pyrrolidone, polyvinyl alcohol and the like), solubilizing retarding agents (such as paraffine), reabsorbing agents (such as quaternary salts) and/or adsorbing agents (such as bentonite, kaolin, dicalcium phosphate and the like). Powdery mixtures may be made into granules by first wetting with combining agents such as syrup, starch paste, gum arabicum, cellulose solution or polymer solution followed by a compulsory passing through a sieve. Instead of granulating the powder as such, the powder may be first treated with a tablet machine and then pulverizing the obtained slugs of various forms to give granules.

Granules thus prepared are mixed with lubricants such as stearates, stearic acid, talc, mineral oil and others whereupon it is possible to prevent adherence to each other. Such a lubricated mixture is then compressed to make tablets. Alternatively, the active substances are, without granulation and making into slugs, directly compressed into tablets after mixing with fluidizing inert carriers. Transparent or semitransparent protective coatings comprising closed shellac membrane, coatings of sugar or polymers, and brushing up coatings comprising waxes may also be used.

Other preparation forms for oral administration such as solutions, syrups, elixers, and the like may also be in dosage unit form in which its definite amount contains definite amounts of pharmaceutically active substance. Syrups are manufactured by dissolving a compound in a suitable aqueous solution of sweetening agent and perfumes. Elixers are prepared by the use of non-toxic alcoholic carriers. Suspensions are prepared by dispersing the compound in non-toxic carriers. If necessary, solubilizing agents and emulsifying agents (such as ethoxylated isostearyl alcohols, polyoxyethylene sorbitol esters. etc.), preservatives, seasoning agents (such as peppermint oil, saccharines, etc.) and others may also be added.

If necessary, dosage unit forms for oral administration may be made into microcapsules. Said form may also be coated and embedded in polymers or wax so that prolongation of acting time or sustained released effect can result.

Parenteral administration can be effected by the use of liquidal dosage unit forms such as solution or suspension suitable for subcutaneous, intramuscular or intravenous injections. They are manufactured first by suspending or dissolving a definite amount of the compound in non-toxic liquid carriers suitable for each injection purpose such as aqueous or oily medium and then by sterilizing said suspension or solution. Alternatively, a definite amount of the compound is taken into vials and then the vial together with the contents are sterilized and sealed. In order to make the substance dissolved or mixed immediately before administration, preliminary or auxiliary vials or carriers may be prepared in addition to pulverized or lyophilized effective constituent. In order to make the injection solution isotonic, non-toxic salt or a solution thereof may be added thereto. Further, stabilizers, preservatives, emulsifiers and the like may be simultaneously applied.

Rectal administration may be conducted through the use of suppositories in which the compound is mixed with a lower melting solid (which is soluble or insoluble in water) such as, for example, polyethylene glycol, cacao butter, higher esters (such as myristyl palmitate) or a mixture thereof.

Pharmaceutical preparations containing the present invention compounds may be mixed with other pharmaceuticals than the present invention compounds such as, for example, other anti-arrhythmic agents, hypotensive agents, blood vein dilating agents, anti-arteriosclerotic agents, etc., or may be jointly used therewith.

The following reference examples illustrate the production of starting materials used in the processes of the present invention:

REFERENCE EXAMPLE A

Ethyl 4-diisobutylaminobutyrate

To 180 ml of xylene were added 176 grams of ethyl gamma-chlorobutyrate, 302.2 grams of diisobutylamine and 6.0 grams of sodium iodide and the mixture was heated to reflux on an oil bath of 120° to 140° C. for 62 hours. After cooling, salts separated out therefrom were removed by filtration, the filtrate was washed with ether, concentrated, and the residue was distilled in vacuo to give 112 grams of the colorless oily product, b.p. 102-6° C./2 mmHg.

REFERENCE EXAMPLE B

Gamma-diisobutylaminobutyrophenone

To 80 ml of dimethylformamide were added 31.0 grams of gamma-chlorophenone ethylene ketal, 21.2 grams of diisobutylamine and 14.2 grams of potassium carbonate and the mixture was heated on an oil bath of 120° C. for 24 hours with stirring. After cooling, inorganic salt separated out therefrom was removed by filtration, the filtrate was washed with ether and then with water, then 2% hydrochloric acid solution was added to the organic solvent layer, and acid-soluble substances were extracted therefrom. The acidic solution was heated at 70° C. for 30 minutes to hydrolyze, then neutralized with an aqueous solution of sodium hydroxide with cooling, and the oil separated therefrom was extracted with ether. The extract was washed with water, dried with magnesium sulphate, and ether was evaporated therefrom. The residue (19.7 grams) was distilled in vacuo to give 16.3 grams of colorless oily product, b.p. 143-5° C./1 mmHg.

Similarly was prepared gamma-diisobutylamino-p-fluorobutyrophenone, colorless oil, b.p. 160-2° C./2 mmHg.

The anti-arrhythmic action of the 4-mono- and di-isobutylaminobutanol derivatives of the present invention as well as the low toxicity of such compounds are illustrated by the following data.

Action Against Arrhythmia in Mice Caused by Aconitine

A method by Nwangwu, et al (P.U. Nwangwu, T.L. Holcslow and S.J. Stohs: Arch. int. Pharmacodyn. 229, 219–226, 1977) was partly modified and the experiment was carried out. ddY-Male mice weighing 25 to 30 grams were used. One group was composed of four mice.

Arrhythmia was induced by infusion of aconitine at a concentration of 5 μg/ml in saline into a tail vein at the rate of 0.25 ml/min using a perfusion pump in mice anesthetized with Nembutal. Test drugs were administered orally or intraperitoneally 30 minutes prior to the start of infusion of aconitine. Incidentally, lidocaine was given intraperitoneally 15 minutes prior to administration of aconitine.

The status of arrhythmia was judged by an electrocardiographic recording (lead II) and, when the onset time of the arrhythmia was delayed more than "average time of untreated group plus 2SD", it was judged to have antiarrhythmic action. Then $ED_{50}$ values were calculated by Weil's method from the effective rate at each dosage level. The results are given in Table 1.

Arrhythmia in Dogs Caused by Digitalis

Beagle dogs weighing 10 to 14 kg were used. They were anesthetized with Nembutal and digoxin was given intraveneously in a dose of 0.10 to 1.5 mg/kg to induce arrhythmia. The arrhythmia was judged by an electrocardiographic recording (lead II) and, when there was an appearance of descending or ascending big QRS complex, it was judged that ventricular arrhythmia appeared. When the ventricular arrhythmia appeared continuously after digoxin administration, test drugs were given intraveneously and the efficacy ratio and duration of the action were observed. The results are given in Table 2.

Action Against Ventricular Arrhythmia Following Coronary Occlusion in Dogs

Beagle dogs weighing 8 to 12 kg were used. Under morphine and Nembutal anesthesia, the chest of dogs was opened or thoracotomized at the fifth intercostal space and the left anterior descending artery was ligated in two steps according to the method of Harris (S.A. Harris: Circulation, Vol. 1, pg. 1318, 1950).

At about 24 hours after the occlusion, four limbs of the dogs were fixed not so tightly under non-anesthetized condition and, at the standing position, EEG recordings were done by standard limb leads for about one hour. Test drugs were given orally when the arryhthmia appeared at the rate of more than 90% of total heart rate. Marked inhibition of ventricular arrhythmia was observed in 3 dogs out of 5 at a dose of 30 mg/kg after oral administration of 4-diisobutylamino-1,1-diphenyl-1-butanol (Example 1). Marked inhibition was also observed in 2 dogs out of 3 at a dose of 30 mg/kg after oral administration of 1,1-diphenyl-4-isobutylamino-1-butanol (Example 10). Similar effects were observed at the same dose of disopyramide, but the present compounds showed much longer action and, even after 24 hours, marked inhibitory effect was still observed.

Toxicities of the present invention compounds were low in all cases. $LD_{50}$ values by oral administration to mice were not more than 1000 mg/kg.

TABLE 1

| Action Against Arrhythmia in Mice Caused by Aconitine | | |
|---|---|---|
| | $ED_{50}$ (mg/kg) | |
| Drugs Applied | p.o. | i.p. |
| 4-Diisobutylamino-1,1-diphenyl-1-butanol (Example 1) | 17.7 | 14.9 |
| 1,1 Diphenyl-4-isobutylamino-1-butanol (Example 10) | 20.3 | 11.5 |
| Disopyramide | 29.7 | 12.5 |
| Lidocaine | — | 35.4 |

TABLE 2

| Action Against Arrhythmia Caused by Digitalis | | | |
|---|---|---|---|
| Drugs Applied | Dose | Efficacy Ratio | Duration of Action |
| 4-Diisobutylamino-1,1-diphenyl-1-butanol (Example 1) | 2 mg/kg | 62.5% | 515 seconds |
| (the same) | 1 | 50.0 | 400 |
| 1,1-Diphenyl-4-isobutylamino-1-butanol (Example 10) | 2 | 58.7 | 500 |
| Disopyramide | 2 | 57.1 | 365 |
| Lidocaine | 2 | 50.0 | 350 |

The following non-limitative examples more particularly illustrate the present invention:

EXAMPLE 1

4-Diisobutylamino-1,1-diphenyl-1-butanol maleate and hydrochloride.

(a) An ethereal solution of phenyl lithium was prepared from 55.7 grams of metal lithium, 629.6 grams of bromobenzene and 1.9 liters of ether and 361.4 grams of ethyl 4-diisobutylaminobutyrate was dropped therein, stirred and inner temperature kept no higher than 25° C. When dropping was completed, the reaction mixture was heated to reflux for about 20 minutes and ether was evaporated therefrom. The residue was dissolved in 1.6 liters of benzene, the solution was washed with water, dried with sodium sulfate and benzene was removed therefrom. The residue (593.9 grams) was dissolved in acetone and allowed to stand after adding maleic acid to afford 4-diisobutylamino-1,1-diphenyl-1-butanol maleate which was collected by filtratation followed by recrystallization from acetone to give 509.4 grams (73%) of colorless needles, m.p. 106–9° C.

Elementary analysis calculated for $C_{24}H_{35}NO \cdot C_4H_4O_4$:

C 71.61, H 8.37, N 2.98; Found: C 71.42, H 8.36, N 2.88%.

IR (KBr) cm$^{-1}$: 3450, 2960, 2800–2200, 1700, 1580, 1480, 1380, 1360, 880, 765, 755, 715, 700.

NMB (d$_6$-DMSO)δ: 0.90 (12H, d, J=6.4 Hz), 1.57 (2H, m), 1.91 (2H, m), 2.29 (2H, m), 2.78 (4H, m), 3.06 (2H, m), 5.71 (1H, m), 6.05 (2H, S), 7.15–7.48 (10H, m), 8.3 (1H, br).

Hydrochloride melted at 131° C. (recrystallized from acetone).

(b) To 5 ml of anhydrous tetrahydrofuran was added 0.41 grams of magnesium, a mixture of 0.1 gram of iodine and 1.0 gram of 3-diisobutylaminopropyl chloride was dropped in with stirring in an argon atmosphere, and the mixture was heated gradually up to refluxing. When the reaction started, a solution of 2.1 grams of 3-diisobutylaminopropyl chloride in 15 ml of anhydrous tetrahydrofuran was dropped in and, after the dropping was completed, the mixture was heated to reflux for three hours. After cooling, a solution of 1.82 grams of benzophenone in 5 ml of anhydrous tetrahydrofuran was dropped in, the mixture was stirred at room temperature for one hour and heated to reflux for another one hour to complete the reaction. The reaction solution was concentrated to about half the volume in vacuo, to the residue was added aqueous solution of ammonium chloride with cooling, then extracted with ethyl acetate, and the extract was washed with water. To the organic solvent layer was added 2% hydrochloric acid, substances soluble in acid were extracted, the extract was neutralized with sodium bicarbonate, oil separated out thereby was extracted with ethyl acetate, the extract was washed with water, dried, and concentrated. The concentrate was dissolved in acetone and the solution was allowed to stand after addition of maleic acid to afford 4-diisobutylamino-1,1-diphenyl-1-butanol maleate. This was collected by filtration and recrystallized from acetone to afford 2.6 grams of colorless needles, m.p. 106–9° C.

EXAMPLE 2

4-Diisobutylamino-1,1-bis(4-chlorophenyl)-1-butanol maleate.

To 2 ml of dry ether was added 0.73 gram of magnesium, the mixture was stirred with warming at 35° C., a solution of 4.79 grams of p-bromochlorobenzene in 25 ml of ether was dropped therein during 15 minutes, the mixture was heated to reflux for about 30 minutes, and stirred at room temperature for one hour and thirty minutes. Then a solution of 2.43 grams of ethyl 4-diisobutylaminobutyrate in 10 ml of ether was dropped in during 10 minutes, the mixture was stirred at room temperature for one hour, cooled, decomposed with a mixture of 40 ml of ice water and 40 ml aqueous solution of ammonium chloride, 10% hydrochloric acid was added to the ether layer to extract acid-soluble substances, the acidic extract was neutralized with sodium bicarbonate, oil separated out thereby was extracted with ether, the extract was washed with water, dried with magnesium sulfate, and ether was evaporated therefrom. The residue (4.2 grams) was subjected to silica gel column chromatography to give purified colorless oily product in 3.0 grams yield. This oily product was crystallized by converting to maleate and recrystallized from acetone to give 1.86 grams of 4-diisobutylamino-1,1-bis(4-chlorophenyl)-1-butanol maleate, m.p. 89° C.

Elementary analysis calculated for $C_{24}H_{33}Cl_2 NO \cdot C_4H_4O_4$: C 62.45, H 6.93, N 2.60; Found: C 62.30, H 7.23, N 2.50%.

IR (KBr) cm$^{-1}$: 3300–3450, 2250–2800, 1590, 1490, 1385, 1355, 1200, 1195, 1015.

EXAMPLE 3

4-Diisobutylamino-1-(4-fluorophenyl)-1-phenyl-1-butanol maleate.

Gamma-diisobutylamino-p-fluorobutyrophenone (2.93 grams) was dissolved in 10 ml of anhydrous tetrahydrofuran, a solution of phenylmagnesium bromide in tetrahydrofuran (2 moles/liter) (6 ml) was dropped therein during 5 minutes, and the mixture was stirred at room temperature for 2 hours. The reaction solution was concentrated to half volume, ice and ammonium chloride solution were added to the concentrate, the oily product separated out thereby was extracted with ethyl acetate, the extract was washed with water, dried with magnesium sulfate, and the solvent was evaporated therefrom. The residue (4.0 grams) obtained was crystallized as a maleate and recrystallized from acetone to give 1.57 grams of 4-diisobutylamino-1-(4-fluorophenyl)-1-phenyl-1-butanol maleate, m.p. 88–92° C.

Elementary analysis calculated for $C_{24}H_{34}FNO \cdot C_4H_4O_4$: C 68.97, H 7.86, N 2.87; Found: C 68.79, H 7.91. N 2.95%.

IR (KBr) cm$^{-1}$: 1 3450, 2200–2800, 2585, 1450–1510, 1390, 1355, 1240, 1200, 1170, 1070, 985.

EXAMPLE 4

4-Diisobutylamino-1,1-bis(4-fluorophenyl)-1-butanol maleate.

Grignard reagent was prepared from p-bromofluorobenzene and then made to react and subjected to after-treatments the same as in Example 2 to give 2.24 grams of 4-diisobutylamino-1,1-bis(4-fluorophenyl)-1-butanol maleate, m.p. 104–6° C. recrystallized from acetone-isopropyl ether).

Elementary analysis calculated for $C_{24}H_{33}F_2 NO \cdot C_4H_4O_4$: C 66.52, H 7.38, N 2.97; Found: C 66.41, H 7.51, N 2.92%.

IR (KBr) cm$^{-1}$: 1 3440, 2300–2700, 1600, 1590, 1505, 1465, 1415, 1385, 1355, 1225, 1085, 1015.

EXAMPLE 5

4-Diisobutylamino-1-(4-chlorophenyl)-1-phenyl-1-butanol maleate.

A solution of p-chlorophenylmagnesium bromide in ether was prepared by the same way as in Example 2 and then reacted and after-treated as same as in Example 3 to afford 3.0 grams of 4-diisobutylamino-1-(4-chlorophenyl)-1-phenyl-1-butanol maleate, m.p. 97–100° C. (recrystallized from acetone-isopropyl ether).

Elementary analysis calculated for $C_{24}H_{34}ClNO$. $C_4H_4O_4$: C 66.72, H 7.60, N 2.78; Found: C 66.66, H 7.84, N 2.94%.

IR (KBr) cm$^{-1}$: 1 3420, 2200–2700, 1580, 1490, 1390, 1360, 1200, 1175, 1100, 1070, 1015, 985.

EXAMPLE 6

4-Diisobutylamino-1-(4-methylphenyl)-1-phenyl-1-butanol maleate.

Grignard reagent was prepared from 4-methylphenyl bromide and reacted and after-treated by the same way as in Example 3 to afford 4-diisobutylamino-1-(4-methylphenyl-1-phenyl-1-butanol maleate, m.p. 117–19° C. (recrystallized from acetone).

Elementary analysis calculated for $C_{25}H_{37}NO$. $C_4H_4O_4$: C 72.02, H 8.55, N 2.90; Found: C 71.92, H 8.79, N 2.81%.

IR (KBr) cm$^{-1}$: 3450, 2990, 2700–2300, 1700, 1590, 1480, 1390, 1360.

EXAMPLE 7

4-Diisobutylamino-1,1-bis(4-methylphenyl)-1-butanol maleate.

Grignard reagent was prepared from 4-methylphenyl bromide and then reacted and after-treated by the same way as in Example 2 to give 4-diisobutylamino-1,1-bis(4-methylphenyl)-1-butanol maleate, m.p. 123–4° C. (recrystallized from acetone).

Elementary analysis calculated for $C_{26}H_{39}NO$. $C_4H_4O_4$: C 72.40, H 8.71, N 2.81; Found: C 72.15, H 8.83, N 2.57%.

IR (KBr) cm$^{-1}$: 1 3430, 2980, 2700–2300, 1690, 1615, 1580, 1510, 1460, 1390, 1385, 1355.

EXAMPLE 8

4-Diisobutylamino-1-(4-methoxyphenyl)-1-phenyl-1-butanol maleate.

Grignard reagent was prepared from 4-methoxyphenyl bromide and then reacted and treated by the same way as in Example 3 to give 4-diisobutylamino-1-(4-methoxyphenyl)-1-phenyl-1-butanol maleate, m.p. 75–7° C. (recrystallized from acetone).

Elementary analysis calculated for $C_{25}H_{37}NO_2$. $C_4H_4O_4$: C 69.71, H 8.27, N 2.80; Found: C 69.48, H 8.48, N 2.71%.

IR (KBr) cm$^{-1}$: 1 3400, 2990, 1700, 1610, 1585, 1510, 1470, 1390, 1355, 1255, 1180.

EXAMPLE 9

4-Diisobutylamino-1,1-bis(4-methoxyphenyl)-1-butanol maleate.

Grignard reagent was prepared from 4-methoxyphenyl bromide and then reacted and treated by the same way as in Example 2 to give 4-diisobutylamino-1,1-bis(4-methoxyphenyl)-1-butanol maleate, m.p. 59–61° C. (recrystallized from acetone ether).

Elementary analysis calculated for $C_{26}H_{39}NO_3$. $C_4H_4O_4$: C 66.89, H 8.23, N 2.60; Found: C 66.89, H 8.64, N 2.60%.

IR (KBr) cm$^{-1}$: 3400, 2980, 1700, 1610, 1590, 1510, 1470, 1390, 1355, 1255, 1180.

EXAMPLE 10

1,1-Diphenyl-4-isobutylamino-1-butanol (maleate).

(1) Manufacture of ethyl 4-hydroxy-4,4-biphenylbutyrate

To 10 ml of dry tetrahydrofuran were added 7.2 grams of magnesium and one leaf of iodine and a solution of 38.8 grams of bromobenzene in 200 ml of dry tetrahydrofuran was dropped therein with stirring and refluxing. After dropping was completed, the stirring was continued for about one hour to prepare Grignard reagent. To 100 ml of dry tetrahydrofuran was added 34.0 grams of ethyl 3-benzoylpropionate and then the Grignard reagent prepared above was dropped thereinto with cooling (at 0° C. in an ice bath) and stirred. After the dropping was completed, the mixture was stirred for another hour at the same temperature and for one more hour at room temperature. Ice and ammonium chloride solution were added to the reaction solution, extracted with ether, the ethereal extract was washed with water, dried with magnesium sulfate, and evaporated in vacuo to give 47 grams of pale orange colored oil. IR (Neet) cm$^{-1}$: 3500, 1780, 1735, 1695.

(2) 1,1-Diphenyl-3-N-isobutylcarbamoyl-1-propanol

To 300 ml of xylene were added 37 grams of crude ethyl 4-hydroxy-4,4-biphenyl obtained in (1) and 15 ml of isobutylamine and the mixture was heated with stirring at 100° to 110° C. in an oil bath for 8 hours. After the reaction was completed, xylene was evaporated therefrom in vacuo and the oily residue was purified by silica gel column chromatography (using 150 grams of silica gel followed by eluting with chloroform) to give 9.0 grams of crystals which were recrystallized from isopropyl ether to afford 6.5 grams of colorless crystals, m.p. 107.0° C. Elementary analysis calculated for $C_{20}H_{25}NO_2$: C 77.14 H 8.09, N 4.50; Found: C 77.16, H 8.50, N 4.43%. IR (KBr) cm$^{-1}$: 3310, 3080, 1635, 1570, 1450, 1275, 1235, 1065, 1022, 765, 760, 705. NMR (CDCl$_3$)δ: 0.87 (6H, d, J =6.0 Hz), 1.61–1.81 (1H, m), 2.22 (2H, t, J=6.4 Hz), 2.63 (2H, t, J=6.4 Hz), 3.02 (2H, t, J=6.4 Hz), 5.44–5.62 (1H, bm), 7.13–7.38 (6H, m), 7.38–7.50 (4H, m).

(3) 1,1-Diphenyl-4-isobutylamino-1-butanol (maleate)

Lithium aluminum hydride (3.27 grams) was added to 100 ml of dry tetrahydrofuran and, with stirring at room temperature, 13.4 grams of 1,1-diphenyl -3-N-isobutylcarbamoyl-1-propanol obtained in (2) dissolved in 50 ml of dry tetrahydrofuran was dropped therein. After the dropping was completed, the mixture was heated to reflux for 14 hours with stirring. After cooling, 4 ml of ethyl acetate and 2 grams of ice were added to the reaction solution. Then 300 ml of ether was added thereto and the mixture was stirred for about 30 minutes. Ether solution was separated therefrom by decantation and the residue was dried with magnesium sulfate. Ether was evaporated therefrom in vacuo to give 12.6 grams of colorless oil. This was dissolved in 200 ml of acetone and the solution was allowed to stand after addition of 4.2 grams of maleic acid, the resulting 1,1-diphenyl-4-isobutylamino-1-butanol maleate separated out therefrom was collected by filtration and recrystalized from a mixture of methanol and ether to give 12.2 grams of colorless crystals. M.p. 173° to 175° C. Elementary analysis calculated for $C_{20}H_{27}NO\cdot C_4H_4O_4$: C 69.71, H 7.56, N 3.39; Found: C 69.89, H 7.57, N 3.38%. IR (KBr) $cm^{-1}$: 3270, 3065, 2700-1740, 1490, 1370, 1220, 1180, 1065, 990, 870, 755, 700. NMR (CDCl$_3$)δ: 1.01 (6H, d, J=8 Hz), 1.79 (2H, m), 1.90-2.22 (1H, m), 2.53 (2H, t, J=6 Hz), 2.68 (2H, d, J=8 Hz), 3.04 (2H, t, J=6 Hz), 6.16 (2H, s), 7.16-7.46 (10H, m). Both IR and NMR data given here are those for the maleate.

What we claim is:

1. A method of treating arrhythmias in humans and animals which comprises administering to a human or animal in need thereof an anti-arrhythmic amount of a compound of the formula (I):

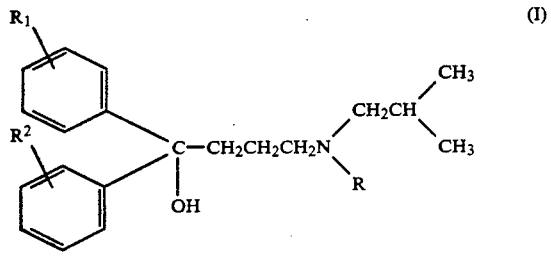

or a pharmaceutically acceptable salt thereof wherein $R^1$ and $R^2$ are the same or different and each is selected from the group consisting of hydrogen, halo, hydroxyl, alkyl of 1 to 4 carbon atoms and alkoxy of 1 to 4 carbon atoms and R is hydrogen or isobutyl, in combination with a pharmaceutically acceptable carrier.

2. A method according to claim 1 wherein R is hydrogen.

3. A method according to claim 1 wherein R is isobutyl.

4. A method according to claim 1 wherein $R^1$ and $R^2$ are the same or different and each is selected from the group consisting of hydrogen, fluoro, chloro, bromo, hydroxyl, alkyl of 1 to 4 carbon atoms and alkoxy of 1 to 4 carbon atoms.

5. A method according to claim 1 wherein $R^1$ and $R^2$ are the same or different and each is selected from the group consisting of hydrogen, fluoro, chloro, bromo, hydroxyl, methyl, ethyl, propyl, isopropyl, tert-butyl, methoxy, ethoxy and propoxy.

6. A method according to claim 1 wherein the compound is in the form of an acid addition salt wherein said acid addition salt is the hydrochloride, hydrobromide, sulfate, sulfamate, phosphate, acetate, citrate, tartrate, succinate, maleate, fumarate, lactate, malate, gluconate, methanesulfonate, p-toluenesulfonate, benzoate or pamoate.

7. A method according to claim 1 wherein the compound is:
   1,1-Bis(2-chlorophenyl)-4-diisobutylamino-1-butanol,
   1,1-Bis(2-fluorophenyl)-4-diisobutylamino-1-butanol,
   1-(2-Chlorophenyl)-4-diisobutylamino-1-phenyl-1-butanol,
   1-(2-Fluorophenyl)-4-diisobutylamino-1-phenyl-1-butanol,
   1,1-Bis(4-Bromophenyl)-4-diisobutylamino-1-butanol,
   1,1-Bis(4-Hydroxyphenyl)-4-diisobutylamino-1-butanol,
   1-(4-Hydroxyphenyl)-4-diisobutylamino-1-phenyl-1-butanol,
   1,1-Bis(4-tert-butylphenyl)-4-diisobutylamino-1-butanol,
   1,1-Bis(4-ethylphenyl)-4-diisobutylamino-1-butanol,
   1,1-Bis(4-ethoxyphenyl)-4-diisobutylamino-1-butanol,
   4-Diisobutylamino-1,1-diphenyl-1-butanol maleate,
   4-Diisobutylamino-1,1-diphenyl-1-butanol hydrochloride,
   4-Diisobutylamino-1,1-bis(4-chlorophenyl)-1-butanol maleate,
   4-Diisobutylamino-1-(4-fluorophenyl)-1-phenyl-1-butanol maleate,
   4-Diisobutylamino-1,1-bis(4-fluorophenyl)-1-butanol maleate,
   4-Diisobutylamino-1-(4-chlorophenyl)-1-phenyl-1-butanol maleate,
   4-Diisobutylamino-1-(4-methylphenyl)-1-phenyl-1-butanol maleate,
   4-Diisobutylamino-1,1-bis(4-methylphenyl)-1-butanol maleate,
   4-Diisobutylamino-1-(4-methoxyphenyl)-1-phenyl-1-butanol maleate,
   4-Diisobutylamino-1,1-bis(4-methoxyphenyl)-1-butanol maleate, or
   1,1-Diphenyl-4-isobutylamino-1-butanol maleate.

* * * * *